United States Patent
Van Furth et al.

(10) Patent No.: US 12,350,488 B2
(45) Date of Patent: Jul. 8, 2025

(54) SYSTEM AND METHOD FOR INTERMITTENT ELECTRICAL MODULATION

(71) Applicant: ACADEMISCH ZIEKENHUIS LEIDEN (H.O.D.N. LUMC), Leiden (NL)

(72) Inventors: Wouter R Van Furth, Leiden (NL); Nienke R. Biermasz, Leiden (NL); Amir H. Zamanipoor Najafabadi, Leiden (NL)

(73) Assignee: ACADEMISCH ZIEKENHUIS LEIDEN (H.O.D.N. LUMC), Leiden (NL)

( * ) Notice: Subject to any disclaimer, the term of this patent is extended or adjusted under 35 U.S.C. 154(b) by 767 days.

(21) Appl. No.: 17/293,957

(22) PCT Filed: Nov. 14, 2019

(86) PCT No.: PCT/NL2019/050745
§ 371 (c)(1),
(2) Date: May 14, 2021

(87) PCT Pub. No.: WO2020/101493
PCT Pub. Date: May 22, 2020

(65) Prior Publication Data
US 2022/0001170 A1    Jan. 6, 2022

(30) Foreign Application Priority Data

Nov. 14, 2018   (NL) ..................................... 2021998

(51) Int. Cl.
*A61N 1/05*    (2006.01)
*A61N 1/36*    (2006.01)
*A61N 1/375*   (2006.01)

(52) U.S. Cl.
CPC ......... *A61N 1/0539* (2013.01); *A61N 1/0534* (2013.01); *A61N 1/3606* (2013.01); *A61N 1/36071* (2013.01); *A61N 1/37518* (2017.08)

(58) Field of Classification Search
CPC .............. A61N 1/0539; A61N 1/37518; A61N 1/0534; A61N 1/3606; A61N 1/36071; A61N 1/36017
See application file for complete search history.

(56) References Cited

U.S. PATENT DOCUMENTS

| | | | |
|---|---|---|---|
| 5,735,817 | A | 4/1998 | Shantha |
| 5,792,100 | A | 8/1998 | Shantha |

(Continued)

FOREIGN PATENT DOCUMENTS

| | | |
|---|---|---|
| AU | 2015203577 A1 | 7/2015 |
| CA | 2653442 A1 | 11/2007 |

(Continued)

OTHER PUBLICATIONS

International Search Report from corresponding PCT Application No. PCT/NL2019/050745, dated Jan. 30, 2020.

(Continued)

*Primary Examiner* — Tammie K Marlen
*Assistant Examiner* — Aya Ziad Bakkar
(74) *Attorney, Agent, or Firm* — Viksnins Harris Padys Malen LLP

(57) ABSTRACT

The present invention relates to a system and method, in which a distal end of an electrode is implanted in an organ, such as a pituitary gland, for intermittent electrical stimulation thereof and a proximal end of the electrode is provided with a connection plug, a distal end of which can be attached to a bone adjacent the organ, such an anterior wall of the sphenoid sinus/vomer, and a proximal end of which can be (Continued)

reversibly connected electrically to a wire that is connected electrically to a source of electrical stimulation for the organ.

20 Claims, 7 Drawing Sheets

(56) References Cited

U.S. PATENT DOCUMENTS

| | | | |
|---|---|---|---|
| 6,013,028 | A | 1/2000 | Jho et al. |
| 2008/0255634 | A1 | 10/2008 | Jaax et al. |
| 2011/0160623 | A1 | 6/2011 | Shalev |
| 2011/0295331 | A1* | 12/2011 | Wells .................. A61N 5/0601 607/3 |
| 2012/0203318 | A1 | 8/2012 | Mann et al. |
| 2012/0323214 | A1 | 12/2012 | Shantha |
| 2014/0214120 | A1 | 7/2014 | Simon et al. |
| 2015/0174406 | A1* | 6/2015 | Lamensdorf ....... A61N 1/36057 607/62 |

FOREIGN PATENT DOCUMENTS

| | | | |
|---|---|---|---|
| CN | 201153979 | Y | 11/2008 |
| CN | 106419897 | A | 2/2017 |
| NL | 2019909 | B1 | 5/2019 |
| WO | WO-2015013252 | A1 * | 1/2015 ............ A61M 31/00 |
| WO | WO-2017/095288 | A1 | 6/2017 |

OTHER PUBLICATIONS

Search Report from corresponding Netherlands Patent Application No. 2021998, dated Mar. 13, 2019.

International Preliminary Report on Patentability (IPRP) from corresponding PCT Application No. PCT/NL2019/050745, dated May 18, 2021.

Office Action from corresponding Chinese Application No. 201980075430.0, dated Sep. 8, 2023.

\* cited by examiner

SYSTEM AND METHOD FOR INTERMITTENT ELECTRICAL MODULATION

CROSS-REFERENCE TO RELATED APPLICATIONS

This application is a national phase application of PCT Application No. PCT/NL2019/050745, filed on 14 Nov. 2019, which claims priority to Netherland Patent Application No. 2021998, filed on 14 Nov. 2018. The entire disclosure of the applications identified in this paragraph is incorporated herein by references.

FIELD OF THE INVENTION

The present invention relates to a system and method for providing intermittent electrical stimulation within a body of a mammal patient, particularly to the pituitary gland, pituitary stalk, basal ganglia and/or hypothalamus of the brain of the mammal.

BACKGROUND OF THE INVENTION

It is known to implant an electrode coupled to a source of electrical pulses, in a patient's organ to stimulate the organ. For example, electrical stimulation of a patient's brain can give relief to the symptoms of, for example, Parkinson's disease, depression and compulsive disorders.

Electrical stimulation for neuro-modulation within the body of a mammalian patient typically has involved patterns of continuous stimulation over 24 hours per day. Pulse generators with their power sources have therefore been implanted within the body, to avoid having an open connection between implanted electrodes and external hardware. Such an open connection has, however, carried a significant risk of infection of the body and limited the patient's freedom of movement.

However, electrical stimulation of the pituitary gland of a mammalian patient can be intermittent, with short periods of stimulation, alternated with longer periods of non-stimulation. For example, intermittent electrical stimulation can be used to induce enhanced ACTH-secretion from the anterior lobe of the pituitary gland as a treatment for the side effects of auto-immune diseases such as Multiple Sclerosis, infantile spasms, proteinuria in nephrotic syndrome, rheumatoid arthritis, dermatomyositis/polymyositis, systemic lupus erythematosus, or symptomatic sarcoidosis.

Similarly, intermittent electrical stimulation of the posterior lobe of the pituitary gland to stimulate the descending axons of the nuclei of the anterior hypothalamus, and induce oxytocin and vasopressin release, can be used as an adjuvant treatment for oncological pain, anxiety disorders, or post-traumatic stress disorder.

Implantation of pulse generators with their batteries has had disadvantages when only used for intermitted treatments, such as requiring additional surgery with resulting discomfort and risks, involving additional costs of the pulse generators and their batteries, involving limited battery lives necessitating replacement surgery, involving more difficulties to adjust stimulation settings for each specific stimulation session, and requiring more difficult to update software.

In co-pending Netherlands patent application no. 2019909, a solution has been provided to the problem of providing electrical pulses directly to the pituitary gland, or to the pituitary stalk and hypothalamus via the pituitary gland without having to insert an implantable electrode through the hard brain membrane, bone and mucous membrane of the nasal cavity. This solution is a system for providing electrical pulses directly to a pituitary gland of a mammalian patient or to a pituitary stalk or to a hypothalamus of the mammalian patient via the pituitary gland, using a catheter that has a distal end that is movable distally through blood vessels, in an endovascular route, of the patient and then into and through a sinus cavernosus of the patient and that contains an action member, a distal end of which is movable distally within the catheter and that includes an implantable electrode, the electrode having a distal end that can move distally, within the catheter, through the endovascular route and then into and through the sinus cavernosus; and then distally out of the catheter through an opening in the distal end of the catheter and then through a perforation in a medial wall of the sinus cavernosus to the pituitary gland and then to and into the pituitary gland.

However, there has been a problem in providing intermittent electrical power to an electrode, when implanted in an organ of a patient. Previous solutions have not been entirely satisfactory. For example, electrical stimulation of a pituitary gland via the trans-sphenoidal route, as described in U.S. Pat. No. 5,792,100, has required that a device be inserted trans-sphenoidal for every stimulation session. In US 2014/0214120 A1, for electrical stimulation of a sphenopalatine ganglion, a pulse generator has had to be implanted intranasal and power has had to be wirelessly transmitted from an external source.

However, maintaining an electrical connection through the surgical route used to insert the electrode may entail unnecessary line connections. Alternatively, when equipping the electrode with a sender and receiver unit and a source of energy in situ requires larger implants than may be desirable.

A simpler, and in particular a more easily accessible, system has been sought for providing intermittent electrical power to an electrode implanted in a pituitary gland.

SUMMARY OF THE INVENTION

This invention relates to a system and method, in which a distal end of an electrode is implanted in an organ, such as a pituitary gland, of a mammalian patient for intermittent electrical stimulation thereof and a proximal end of the electrode is provided with a connection plug, a distal end of which can be attached to a bone adjacent the organ, such an anterior wall of the sphenoid sinus/vomer, and a proximal end of which can be reversibly connected electrically to a wire that is connected electrically to a source of electrical stimulation for the organ.

Advantageously, the distal end of the electrode can move: distally, within a catheter, through an endovascular route of the patient and then into and through the sinus cavernosus of the patient; and then distally out of the catheter through an opening in the distal end of the catheter and then through a perforation in a medial wall of the sinus cavernosus to the organ, such as the pituitary gland, of the patient and then to and into the organ.

This invention also relates to a method, wherein the electrode array is provided for interfacing with the organ tissue in situ, the device comprising: a. a deformable array of electrodes comprising a plurality of electrodes in electrical communication with a plurality of deformable electrical interconnects and a connector line; wherein the deformable array of electrodes provides a net bending stiffness of the array low enough that the device is capable of establishing conformal contact with the tissue in situ; and b. a connection plug provided at the proximal end of the connector line of the electrode array provided with a distal end of which can be attached to a bone adjacent the organ, such an anterior wall of the sphenoid sinus/vomer, and a proximal end of which can be reversibly connected electrically to a wire that is connected electrically to a source of electrical stimulation for the organ, or connected to or a device for harvesting electrical energy induced by an external electricity induction- and control unit.

Preferably, the distal end of the electrode array can be introduced by moving it: a. distally, within a catheter, through an endovascular route of the patient and then into and through the sinus cavernosus of the patient; and then b. distally out of the catheter through an opening in the distal end of the catheter and then through a perforation in a medial wall of the sinus cavernosus to the organ, such as the pituitary gland, of the patient and then to and into the organ.

This invention also relates to a method for spatial and temporal electrically interfacing with an organ, preferably brain tissue, more preferably the pituitary gland, the method comprising the steps of: providing an electrode array according to the invention, and electrically contacting at least a portion of the plurality of electrodes with the tissue by conformally contacting a surface of the tissue with the electrode array; and spatio-temporally interfacing the brain tissue with the conformable device to monitor or actuate a spatio-temporal profile over the surface of the brain tissue in electrical contact with the plurality of electrodes; and actuating electrical activity over the brain surface by applying an electric potential of a plurality of individual brain surface locations beneath each electrode of the array of electrodes at a plurality of different locations and/or time points; and/or optionally, monitoring the spatio-temporal electrical brain profile with the device in conformal and electrical contact with a brain surface of a subject, wherein the monitoring comprises detecting an electric potential of a plurality of individual brain surface locations beneath each electrode of the array of electrodes at a plurality of different time points.

BRIEF DESCRIPTION OF THE DRAWINGS

The following exemplary drawings illustrate preferred embodiments of the system and method of this invention. Other objects and features will be apparent from the following description and drawings in which the following figures are as follows.

DETAILED DESCRIPTION OF THE INVENTION

Figure 1:
FIG. 1: MRI showing normal pituitary gland in the sella turcica of the skull of a mammalian patient.

In general, the terms and phrases used herein have their art-recognized meaning, which can be found by reference to standard texts, journal references and contexts known to those skilled in the art. The following definitions are provided to clarify their specific use in the context of the invention.

Herein, the term "electrically interfacing" refers to the ability to monitor and/or generate electrical waveforms on the brain surface in regions underlying the device electrodes.

Herein, the term "brain tissue" refers to brain in the in vivo, in vitro, or the ex vitro environment. The brain may be from a human or a non-human, such as an animal.

Herein, the term "conformable" refers to a device, material or substrate which has a bending stiffness sufficiently low to allow the device, material or substrate to adopt a desired contour profile, for example a contour profile allowing for conformal contact with a surface having a pattern of relief or recessed features. In certain embodiments, a desired contour profile is that of a tissue in a biological environment, for example heart tissue.

Herein, the term "Deformable" is used similar to conformable, and refers to a device, material or substrate can flex, bend, or conform without undue induced strain during deformation, specifically an induced strain below that required to induce mechanical fracture or permanent fatigue. In particular, the element is considered deformable if any induced stress associated with deformation is below the ultimate tensile stress or the yield stress.

Herein, the term "Stretchable" refers to the ability of a material, structure, device or device component to be strained without undergoing fracture. In an exemplary embodiment, a stretchable material, structure, device or device component may undergo strain larger than 0.5% without fracturing, for some applications strain larger than 1% without fracturing and for yet other applications strain larger than 3% without fracturing. As used herein, many stretchable structures are also flexible. Some stretchable structures (e.g., device components) are engineered to be able to undergo compression, elongation and/or twisting so as to be able to deform without fracturing. Stretchable structures include thin film structures comprising stretchable materials, such as elastomers; bent structures capable of elongation, compression and/or twisting motion. Stretchable device components include structures having stretchable interconnects, such as stretchable electrical interconnects.

Herein, the term "electrical communication" refers to an arrangement of two components of a device wherein electrical signal (e.g., current, potential) is passed between the two components. For example, each electrode in the array is electrically connected to a pair of transistors, and the transistors are connected to a current source or sink, and specifically, to a controller. The parts of the device that convey the electrical signal between the electrical components are herein referred to as "interconnects".

The present invention provides a method and apparatus related to electrophysiological stimulation and/or measurements over a complex-shaped biological surface in the brain of a mammal. The present invention also provides implantable electronic devices and devices administered to the surfaces(s) of a target tissue for obtaining electrophysiology data from a brain tissue, and/or for stimulation the brain tissue electrically. Also disclosed are methods of sensing and making measurements in a biological environment, including methods of making in vivo electrophysiology measurements.

In a preferred aspect, the methods provided herein relate to both monitoring and actuating brain tissue. The configuration of the device and electrodes of the device permit sensing or monitoring of electric potential over the brain surface by the electrodes and/or actuation of electric potential over the brain surface by energization of the electrodes.

In a preferred aspect, the methods provided herein may further comprise the step of actuating a spatially and temporally defined electrical profile over the surface of the brain tissue.

The actuation of a profile over the surface of the brain tissue may comprises energizing the plurality of electrodes so that a voltage pattern is generated over the electrode array. In an aspect, each electrode is capable of energization in a time-dependent fashion. In this manner, because there is an electrical connection between each electrode and each brain surface location underlying the electrode, complex spatiotemporal waveforms can be generated on the brain surface from the corresponding time-dependent energization of electrodes.

Preferably, the electrode array comprises a multitude electrodes spaced and located such that they allow for a high temporal resolution control, extremely fine voltage profiles that preferably can rapidly change with time, thereby being suitable for providing high-spatial and temporal spatiotemporal electrical waveforms along the brain surface and underlying regions thereof.

The term "energizing" refers to independently energizable electrodes in the electrode array. This may imply regulating both the magnitude of voltage and the time-dependency of voltage magnitude being independently controlled for each electrode.

In a preferred aspect, the actuating step comprises energizing the plurality of electrodes with a pattern of electric potential having a stimulation profile that stimulates the brain in a pre-emptive manner to cause the neural tissue to be in a refractory state prior to the arrival of the next wave. This prevents the continuation of an ongoing seizure pattern. Other useful actuating steps relate to energization of electrodes to generate a region of high frequency stimulation or depolarization sufficient to at least partially terminate propagation the abnormal waveform, or to generate a polarity profile corresponding to a waveform of normal brain activity.

The devices used in the method may be further characterized by a number of physical parameters. In an aspect, the conformable device is bendable, stretchable, or both bendable and stretchable. The bendable aspect is particularly relevant for applications where the conformable device is at least partially inserted into a brain surface invagination and where the device is folded over a support material to provide two-sided interfacing capability.

Other relevant physical parameters relate to methods having a certain spatial resolution. In an aspect, the spatial resolution is selected from a range that is greater than or equal to 50 μm and less than or equal to 5 mm. Spatial resolution is selected by adjusting the spacing or separation distance between adjacent electrodes, such as an edge-to-edge distance.

In a preferred aspect, the present invention also relates to a system according to the invention, comprising an electrode or electrode array, the distal end of which has one or more contact points for electrical stimulation of endocrine tissue of the pituitary gland, the pituitary stalk or the hypothalamus.

In a further preferred aspect, the present invention also relates to a system according to the invention, comprising an electrode or electrode array, the distal end of which has one or more contact points for electrical stimulation of endocrine tissue of the pituitary gland, the pituitary stalk or the hypothalamus, for treating chronic pain and central sensitization disorders.

In a further preferred aspect, the present invention also relates to a method for treating a central sensitization disorder in a subject in need thereof, comprising a. introducing a system according to the invention and administering to the subject a therapeutically effective electrical impulse through the electrode or electrode array, either with multiple signals, or with a simple mono-pulse between two electrodes. Preferably, the method and system is configured and operable to treat sensitization disorders comprises treating chronic pain.

This may permit to deal with an ongoing and pervasive problem in the medical community is treating patients with chronic pain syndromes. It is well recognized today that chronic pain is fundamentally different from acute pain, also referred to as nociceptive pain, which pain results from a mechanical, chemical, metabolic or inflammatory insult. Central sensitization is a diagnostic target entity that underlies a broad range of phenotypic syndromes, including various chronic musculoskeletal pain, neuropathic pain, and mood and post-traumatic disorders. As used herein, central sensitization means an abnormal state of functioning of the neurons and circuitry of the central pain intensity, perception and modulation systems; due to synaptic, chemical, functional and/or structural changes, in which pain is no longer coupled, as acute nociceptive pain is, to particular peripheral stimuli. Instead, the central nervous system (CNS) initiates, maintains and contributes to the generation of pain hypersensitivity and perception, absent a peripheral stimulus, and ultimately manifests in clinical presentations of phenotypic central sensitivity syndromes (CSS). As used herein, therefore chronic pain and central sensitization represent an overlapping constellation of diagnostic conditions and syndromes. Accordingly, the present invention also relates to a system, wherein the electrode or electrode array is based on the outside of the pituitary gland, and wherein the electrode or electrode array is located at the outside of the membrane enveloping the posterior pituitary stores, and operable for effecting secretion of the endocrine hormones.

In a preferred aspect, the distal end of the electrode is adapted to: electrically stimulate the pituitary gland to produce and secrete adrenocorticotropic hormone (ACTH), antidiuretic hormone (ADH), Oxytocin (OXT), and/or alpha-melanocyte stimulating hormone (MSH); and/or electrically stimulate the pituitary gland to stimulate the magnocellular nuclei of the anterior hypothalamus through axons that descend through the pituitary stalk to the pituitary gland. In a preferred aspect, a distal portion of the electrode or microcannula has a shape memory and thus can form a three-dimensional shape, preferably a coil shape, within or about the pituitary gland, preferably when triggered by remote control.

Preferably this implies inserting specifically configured electrodes that are conformable and provide the ability to stimulate and/or measure complex waveforms over relatively large areas of the brain, and/or selectively stimulating certain areas including in areas requiring high device bendability such as in the pituitary gland.

In a preferred aspect, the subject invention also comprises a method for electrically interfacing with the surface of brain tissue, preferably the pituitary gland tissue, by providing a conformable electrode for interfacing with the tissue in suit, wherein the electrode comprises a deformable substrate and a deformable array of electrodes comprising a plurality of electrodes in electrical communication with a plurality of deformable electrical interconnects.

Preferably, a barrier layer encapsulates at least a portion of the deformable electrical interconnects, wherein the deformable substrate, deformable array of electrodes and the barrier layer provide a sufficiently low bending stiffness of the electrode after introduction into the relevant tissue location to ensure that the electrode establishes and maintains conformal contact with the tissue in situ. Ideally, the deformable array of electrodes is supported by the barrier layer for this purpose, but may also comprise a further stabilising support unit, e.g. a shape memory material frame or support, or any other suitable Preferably, at least a portion of the plurality of electrodes is electrically contacted with the brain tissue, preferably the pituitary gland surface, more preferably located epidurally to the diaphragma sellae, or transdurally to the diaphragma sellae but on the outside of the gland surface, by conformally contacting the conformable device with a surface of the gland or dura surrounding the gland, and interfacing the tissue or dura with the conformable device to monitor and/or actuate a stimulation profile over the surface of the tissue in electrical contact with the plurality of electrodes.

In accordance with the system and method of this invention, an electrode 10, preferably an electrode array, can be securely inserted into an organ of a mammalian patient, or positioned adjacent to an organ, preferably a pituitary gland 12, more preferably its posterior lobe 11 as shown in FIG. 1, and held in or at the organ for prolonged and/or repeated use, e.g., for providing electrical stimulation of the organ. The design and structure of the electrode 10 are not critical and can be conventional for mammalian organ therapies.

Figure 2:
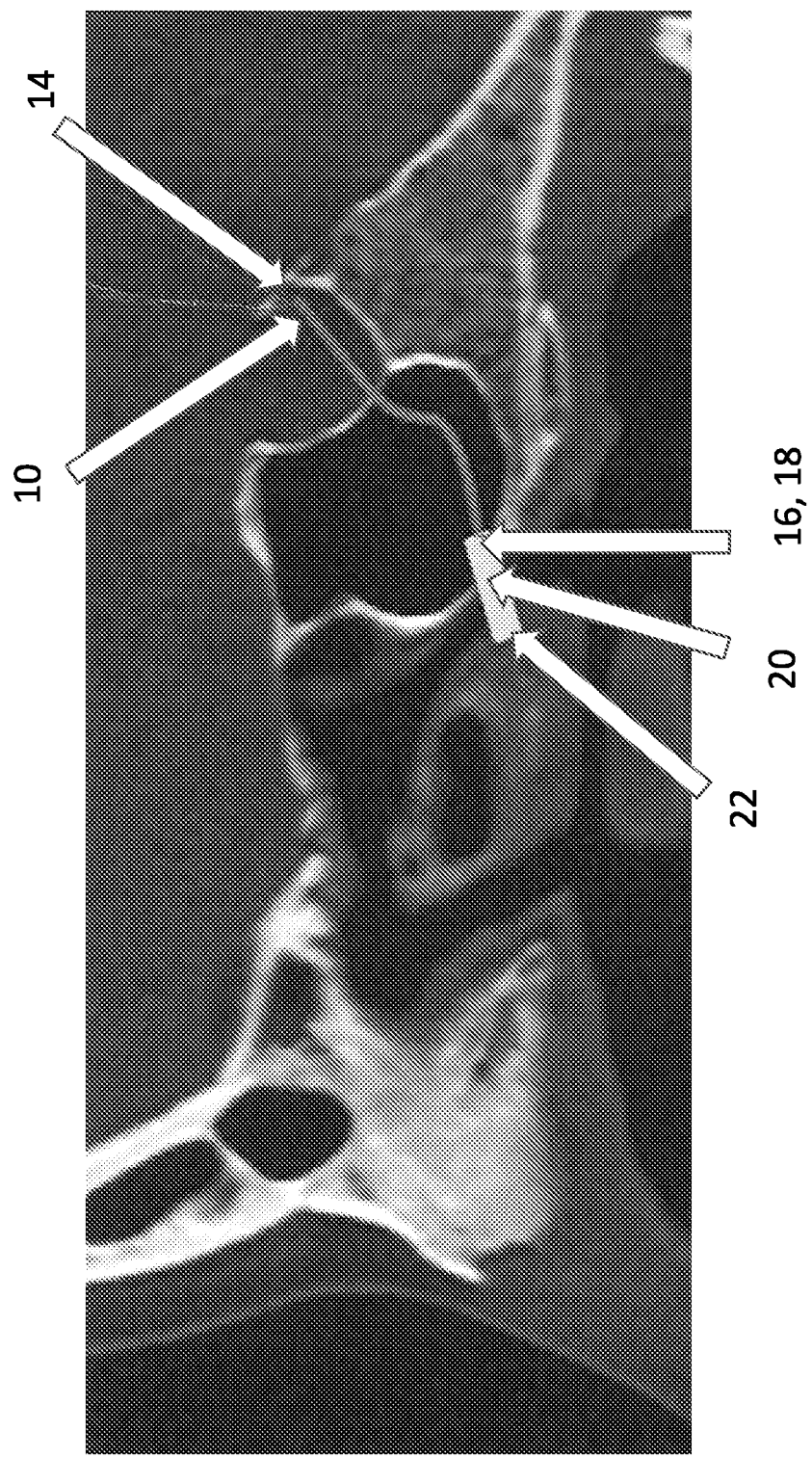
FIG. 2: Schematic MRI showing the pituitary gland of FIG. 1 with the distal end of an electrode extending through an opening in the medial wall of the sinus cavernosus and inserted in the pituitary gland and a terminal connection plug at the proximal end of the electrode.
Figure 3:
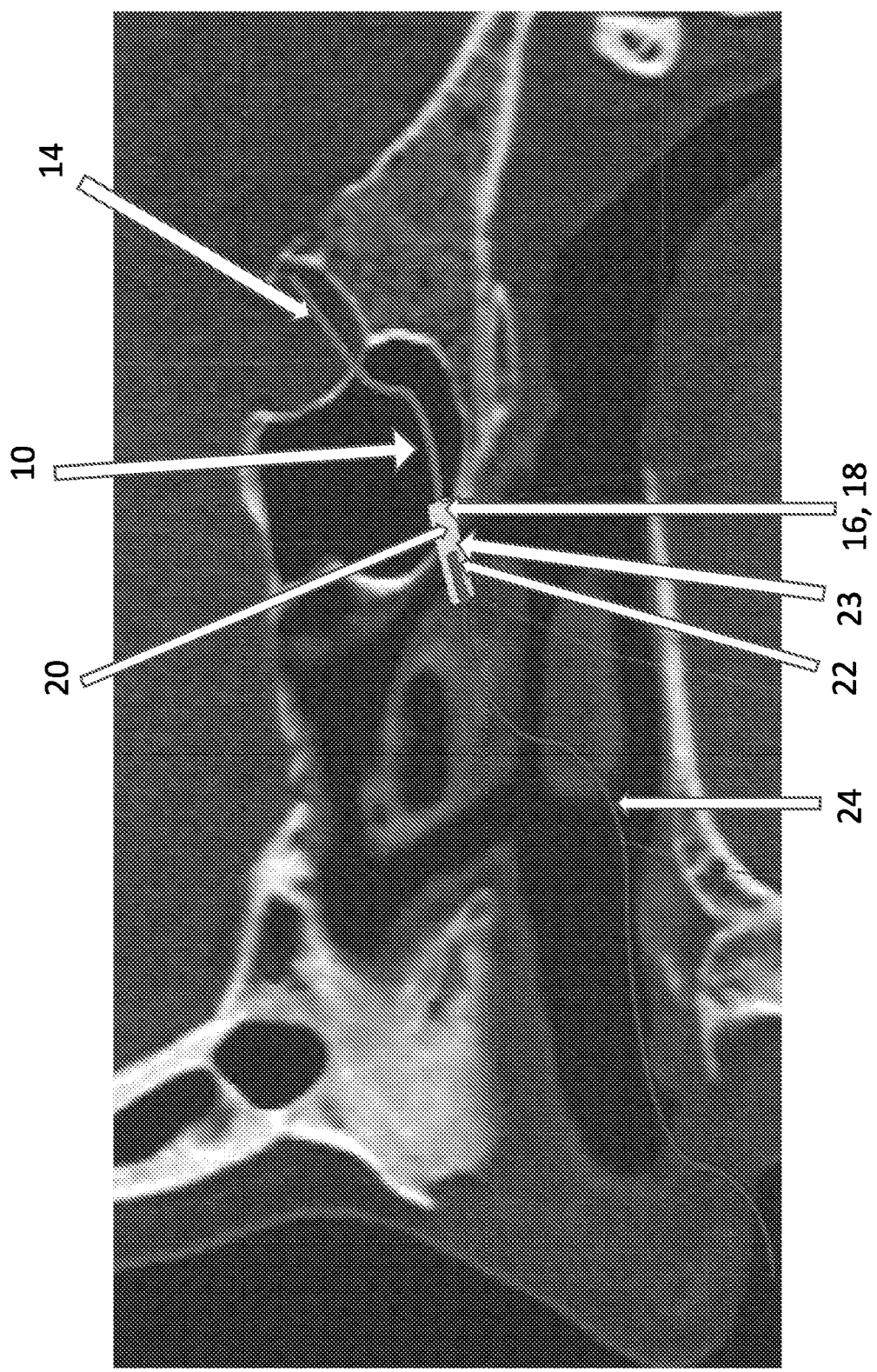
FIG. 3: Schematic MRI showing the pituitary gland and electrode of FIG. 2 with the distal end of the electrode inserted in the pituitary gland, the terminal connection plug at the proximal end of the electrode with a connection wire to an external pulse generator and power source.

As schematically shown in FIGS. 2 and 3, a distal end 14 of the electrode 10 is embedded in the pituitary gland 12. The distal end 14 of the electrode 10 preferably has multiple stimulation points (not shown) embedded in the pituitary gland 12. Embedding the distal end 14 of the electrode in the pituitary gland can be accomplished in any conventional manner, e.g., by surgery, but is preferably accomplished without surgery through a trans-sphenoidal route as described in co-pending Netherlands patent application no. 2019909, which is incorporated herein. In this regard, the electrode 10 is preferably moved distally, within a catheter (not shown), to the inferior or superior petrosal sinus of a mammal and then to the sinus cavernosus of the mammal. Preferably, the electrode is moved, within the catheter, from a vena jugularis via an endovascular route to an inferior or superior petrosal sinus and then to the sinus cavernosus of the mammal. The distal end 14 of the electrode is then moved further distally out of the distal end of the catheter and through a perforation in the medial wall of one of the sphenoid sinuses of the sinus cavernosus, then through the sphenoidal sinus 15 and then through the pituitary gland 12 of the mammal, preferably to its posterior lobe 11, more preferably into its posterior lobe 11.

As also shown in FIGS. 2 and 3, a proximal end 16 of the electrode 10 is connected to a distal end 18 of a terminal connection plug 20. The connection plug 20 is affixed, e.g., by surgery, with a dedicated holder (not shown) to the bone (not shown) of the anterior wall of the sphenoid sinus/vomer. perdural connection plug 20 is accessible through a nostril cavity of the mammal under direct or endoscopic vision. In this regard, the distal end 23 of the wire 24 can be guided into and then through the mammal's nostril cavity to the electrical socket on the proximal end 22 of the connection plug 20. Then, the mammal can be treated by electrically connecting a conventional external pulse generator (not shown) to the electrode 10 implanted in the pituitary gland by connecting the proximal end of the second electrical wire 24 to the pulse generator and connecting the distal end 23 of the second wire 24 to the electrical socket (not shown) on the proximal end 22 of the connection plug 20. Thereby, the proximal and distal ends 14, 16 of the implanted electrode 10 are electrically connected, via the plug 20, to the pulse generator. If desired, the pulse generator, when electrically connected by the wire 24 to the electrode 10, can be carried on the outside of the mammal's body during electrical stimulation of the electrode 10.

If the wire 24 is accidently pulled outwardly of the electrical socket of the connection plug 20 during electrical stimulation of the electrode 10, the pulse generator becomes disconnected from the electrode 10 at the system's most vulnerable point, the proximal end 22 of the connection plug 20. This prevent possible displacement of the electrode 10, even when a pulling stress is placed on the system.

When electrical stimulation of the electrode 10 is to be stopped, the pulse generator can be disconnected from the electrode 10 by removing the distal end 23 of the electrical wire 24 from the electrical socket on the proximal end 22 of the connection plug 20.

When this system is not in use, the proximal end 22 of the connection plug 20 and its socket, will be covered by sphenoid mucosa, and as such protected from the environment. To access the connection plug 20 and its socket again, for the next use of the system for stimulating the pituitary gland of the mammal, the mucosa simply needs to be cut away from the electrical socket at the proximal end 22 of the plug 20. Mucosa is much less sensitive and heals without visible scars when compared to skin.

The sphenoid sinus is accessible via the subcutaneous route for electrodes implanted elsewhere, such as DBS electrodes or vagal nerve electrodes. Thus, the system of this invention can be used for other types of electrical brain stimulation when only discontinuous, intermittent stimulation is required.

Figure 4:
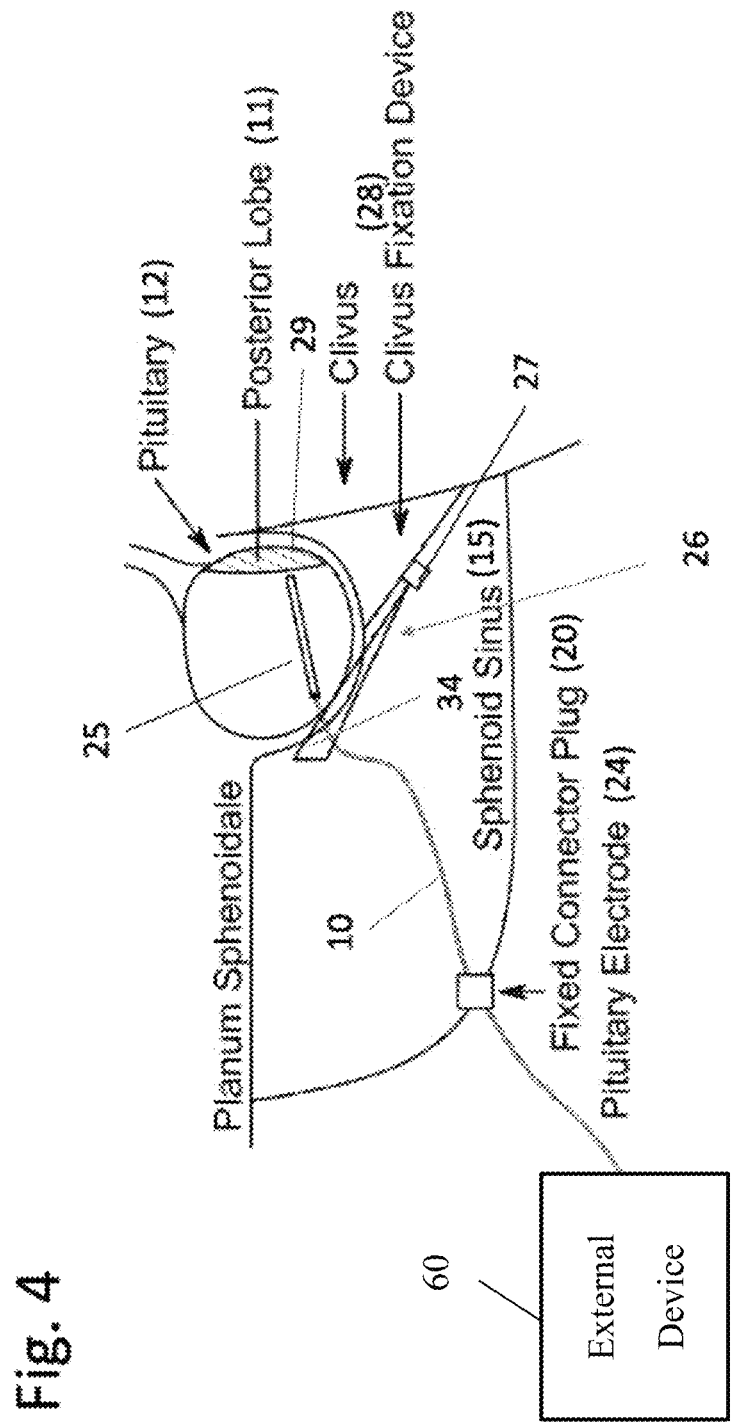
FIG. 4: Schematic showing the electrode of FIGS. 2 and 3 extending through an opening in the medial wall of the sinus cavernosus, then through the sphenoidal sinus, then through a support member, and then through the pituitary gland to its posterior lobe.
Figure 5:
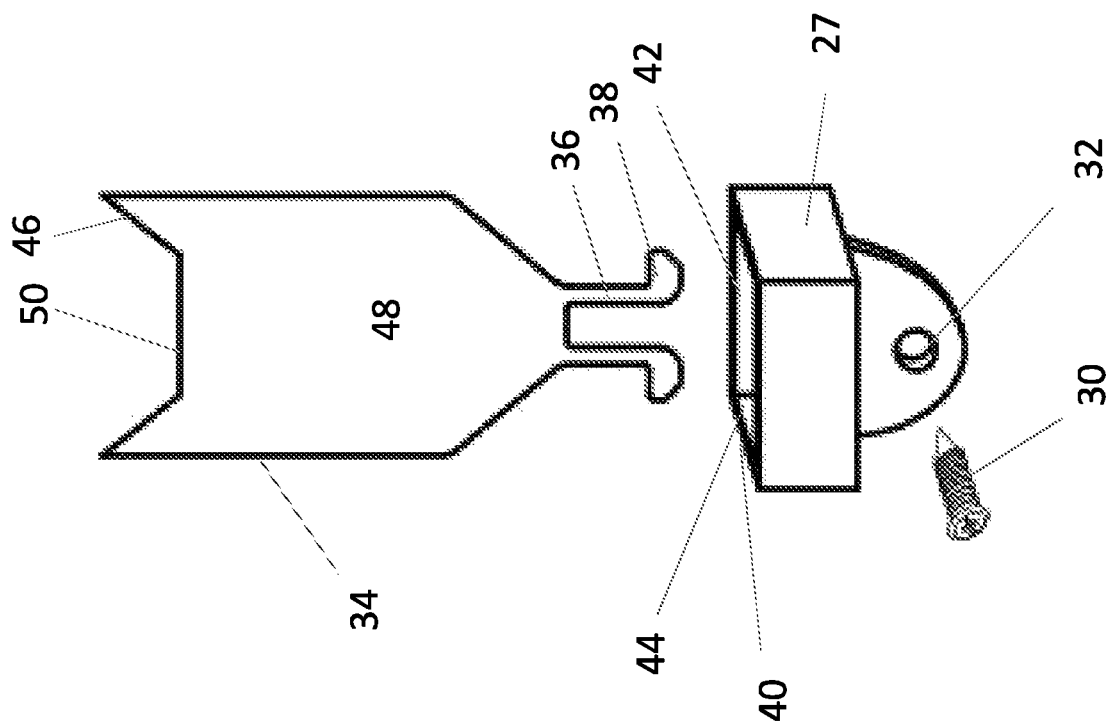
FIG. 5: Exploded schematic of the support member of FIG. 4, showing its shield and anchor.

As shown in FIGS. 4 to 7, distal portions 25 of the electrode 10 are securely, preferably permanently, held in the posterior lobe 11 of the pituitary gland 12 of the mammal by a two-piece semi-rigid support member 26. As shown in FIG. 4, the electrode 10 includes a proximal end connected to the connection plug 20 and the wire 24 includes a distal end connected to the connection plug 20 and a proximal end connected to an external device 60. As shown in FIGS. 4 and 5, a lower portion of the support member 26 is formed by an anchor 27, affixed (e.g., by surgery) to the clivus 28 of one of the sphenoid sinuses of the sinus cavernosus of the mammal. The anchor 27 can be attached to the clivus 28 in any conventional manner but is preferably mounted with a screw 30 extending through a hole 32 in the bottom of the anchor 27 as shown in FIG. 5 and then into the clivus, just below the sella turcica 29 (in which is the pituitary gland) as shown in FIG. 4. As also shown in FIGS. 4 and 5, an upper portion of the support member 26 is formed by a generally planar shield 34, the bottom of which is attached to the top of the anchor 27. The shield 34 is preferably made from a semi-rigid radiopaque and MRI-compatible polymeric material, such as a bio-compatible silicone. The anchor 27 is preferably made from a rigid MRI-compatible plastic material, such as a bio-compatible silicone which can securely hold the shield 34 on the clivus 28.

Figure 6:
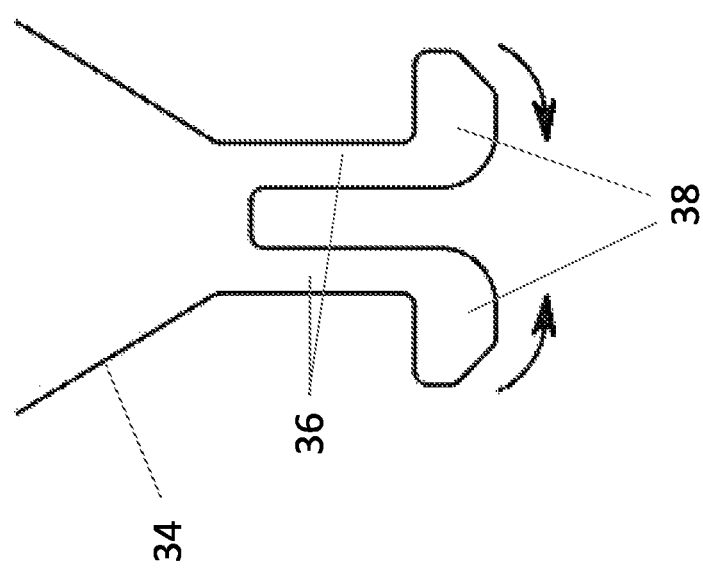
FIG. 6: Schematic detail of a bottom portion of the shield of the support member of FIG. 5.

As shown in FIGS. 5 and 6, a bottom portion of the shield 34 is preferably provided with a pair of downwardly-extending parallel fingers 36, the tips 38 at the bottom ends of which extend away from each other in the same plane. The fingers 36 are sufficiently resilient, so that they move towards each other when their tips 38 are urged together, i.e., pressed towards each other, and so that they move away from each other when their tips are no longer being urged together. As shown in FIG. 5, the top wall 40 of the anchor 26 has an open central portion 42, into which the fingers 36 and their tips 38 can be downwardly inserted while urging their tips together and in which the fingers 36 and their tips 38 can subsequently be securely held by a closed peripheral portion 44 of the top wall 40 after their tips are no longer being urged together.

Figure 7:
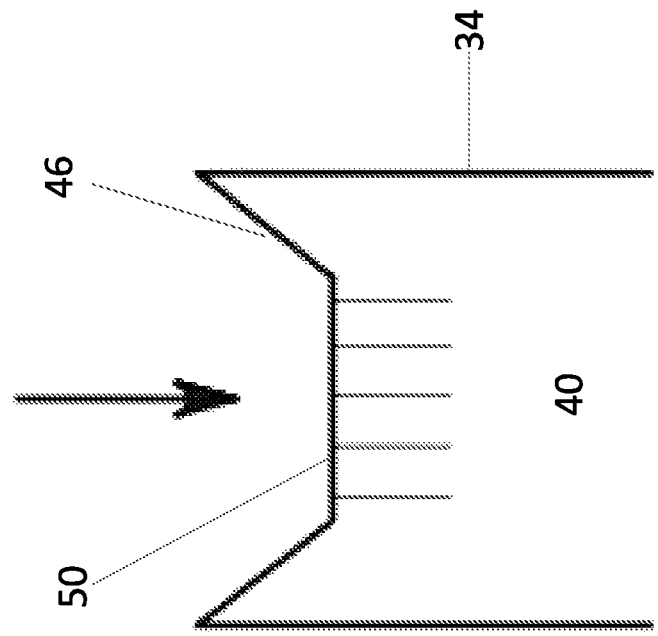
FIG. 7: Schematic detail of an upper portion of the shield of the support member of FIG. 5.

As shown in FIG. 7, a top portion of the shield 34 is preferably provided with a downwardly-extending groove 46 extending through the shield between the side walls 48 on opposite sides of the shield. The bottom 50 of the groove 46 is flat, so that distal portions 25 of the electrode 10 (not shown in FIG. 5) can lie flat on the bottom 50 of the groove as the electrode extends through the sphenoidal sinus 15 into the pituitary gland of the mammal. Preferably, the bottom 50 of the groove 46, containing the inserted electrode, is filled with a biocompatible glue (not shown), to hold distal portions 25 of the electrode 10 securely in place in the bottom 50 of the groove 46.

As shown in FIG. 4, the side wall 48 of the shield 34, adjacent the sella turcica 29, is preferably somewhat curved, concave upwardly from bottom to top, so that the shield fits closely around the curve of the sella turcica.

The invention claimed is:

1. A percutaneous system intended to be fixed in an osseous structure of a mammalian patient for intermittent electrical stimulation, the percutaneous system comprising:
    an electrode or electrode array comprising one or more electrodes including a distal end configured to be implanted in an organ comprising brain tissue of the patient for intermittent electrical stimulation thereof, wherein the organ comprises a pituitary gland, and
    an electric connection means configured to be connected to a proximal end of the electrode or electrode array and configured to be surgically fixed, with a dedicated holder, in an osseous structure of the sphenoid bone, the electric connection means reversibly connected electrically to a source of electrical stimulation for the electrode or electrode array.

2. The system of claim 1, wherein the distal end of the electrode or electrode array is permanently implanted in the organ, and wherein the proximal end of the electrode or electrode array is reversibly connected electrically to the source of electrical stimulation for the organ by a separate electrical connection means or by an induction device.

3. The system of claim 1, further comprising:
    a percutaneous socket coupled to a proximal end of the electric connection means, the socket having a first end comprising a first connector to be connected to the source of electrical stimulation and a second end opposite to the first end, and
    a flexible electric connection member securely fastened to, and extending from the second end of the socket, and securely fastened to, and extending from the electrode.

4. The system of claim 3, wherein the percutaneous socket comprises an anchoring base anchored in the osseous structure.

5. The system of claim 1, further comprising an insulation enclosure comprising biocompatible materials.

6. The system of claim 3, wherein the percutaneous socket is adapted to be connected to an external power supply, and an intermediate connector and the electrode being electrically connected by a flexible intermediate connecting element.

7. The system of claim 1, wherein the distal end of the electrode or electrode array has one or more contact points for electrical stimulation of endocrine tissue of the pituitary gland, the pituitary stalk or the hypothalamus.

8. The system of claim 7, wherein the distal end of the electrode or electrode array is adapted to: electrically stimulate the pituitary gland to produce and secrete adrenocorticotropic hormone (ACTH); ADH, oxytoxin, and/or alpha-melanocyte stimulating hormone (MSH); and/or electrically stimulate the pituitary gland to stimulate the magnocellular nuclei of the anterior hypothalamus through axons that descend through the pituitary stalk to the pituitary gland.

9. The system of claim 8, wherein the electrode or electrode array is based on an outside of the pituitary gland, and wherein the electrode or electrode array is located at an outside of a membrane enveloping the posterior pituitary stores, and operable for effecting secretion of endocrine hormones.

10. The system of claim 9, wherein a distal portion of the electrode or electrode array has a shape memory and thus can form a three-dimensional shape, within, at the outside of the membrane adjacent to, or about the pituitary gland.

11. The system of claim 10, wherein the distal portion of the electrode or electrode array has a shape memory and thus can form a coil shape when triggered by remote control.

12. A method for treating a central sensitization disorder in a subject in need thereof, comprising
    introducing the system according to claim 1, and
    administering to the subject a therapeutically effective electrical impulse through the electrode or electrode array.

13. The method according to claim 12, wherein the central sensitization disorder comprises chronic pain.

14. The system of claim 1, wherein the electrode or electrode array is implanted in the organ via an endovascular route or a transsphenoidal route.

15. A method for intermittent electrical stimulation, comprising:
    implanting a distal end of an electrode or electrode array in an organ comprising brain tissue of a mammalian patient for intermittent electrical stimulation, wherein a proximal end of the electrode or electrode array is provided with a connection plug and the organ comprises a pituitary gland,
    attaching the connection plug to the sphenoid bone, wherein the proximal end of the connection plug is reversibly connected electrically to a wire that is connected electrically to a source of electrical stimulation for the electrode or electrode array.

16. The method of claim 15, wherein the distal end of the electrode or electrode array is permanently implanted.

17. The method of claim 15, wherein the distal end of the electrode or electrode array is implanted in the brain tissue.

18. The method of claim 15, wherein the electrode array is provided for interfacing with an organ tissue in situ, the electrode array comprising:

a deformable array of electrodes comprising a plurality of electrodes in electrical communication with a plurality of deformable electrical interconnects and a connector line;

wherein the deformable array of electrodes provides a net bending stiffness of the electrode array low enough that the electrode array is capable of establishing conformal contact with the organ tissue in situ.

19. The method of claim 15, wherein the distal end of the electrode or electrode array is introduced by moving it:
   a. distally through an endovascular route of the patient and then into and through the sinus cavernosus of the patient; and then
   b. distally through a perforation in a medial wall of the sinus cavernosus to the organ of the patient and then to and into the organ.

20. The method of claim 15, wherein the electrode or electrode array is implanted in the organ via an endovascular route or a transsphenoidal route.

* * * * *